(12) United States Patent
Gao

(10) Patent No.: US 8,832,019 B2
(45) Date of Patent: Sep. 9, 2014

(54) ERROR SIMULATION FOR IMAGE-GUIDED DENTAL IMPLANT TREATMENT PLANNING

(75) Inventor: Fei Gao, Cypress, CA (US)

(73) Assignee: Fei Gao, Cypress, CA (US)

(*) Notice: Subject to any disclaimer, the term of this patent is extended or adjusted under 35 U.S.C. 154(b) by 408 days.

(21) Appl. No.: 13/017,476

(22) Filed: Jan. 31, 2011

(65) Prior Publication Data
US 2012/0197620 A1    Aug. 2, 2012

(51) Int. Cl.
G06Q 50/22    (2012.01)
G06F 19/00    (2011.01)

(52) U.S. Cl.
CPC .......... *G06F 19/3437* (2013.01); *Y10S 128/92* (2013.01); *Y10S 128/922* (2013.01); *Y10S 128/923* (2013.01); *Y10S 128/924* (2013.01); *Y10S 706/919* (2013.01); *Y10S 706/92* (2013.01); *Y10S 706/924* (2013.01)
USPC ............. 706/62; 128/920; 128/922; 128/923; 128/924; 433/171; 433/172; 433/201.1; 706/919; 706/920; 706/924

(58) Field of Classification Search
USPC ......................................................... 706/62
See application file for complete search history.

(56) References Cited

PUBLICATIONS

Vrielinck C et al. Image-based planning and clinical validation of zygoma and pterygoid implant placement in patients with severe bone atrophy using customized drill guides. Preliminary results from a prospective clinical follow-up study. Int J Oral Maxillofac Surg, vol. (32), No. 1 pp. 7-14 [online], 2003 [retrieved on Nov. 19, 2012]. Retrieved from the Internet:<URL:http://www.sciencedirect.com>.*
Spolyar et al., Image Corrected Cephalometric Analysis (ICCA): Design and Evaluation [online], 1993 [retrieved on Dec. 30, 2013]. Retrieved from the Internet:<URL:http://www.google.com/url?sa=t&rct=j&q=&esrc=s&frm=1&source=web&cd=6&ved=0CFQQFjAF&url=http%3A%2F%2Fwww.cpcjournal.org%2Fdoi%2Fpdf%2F10.1597%2F1545-1569(1993)030%253C0528%3AICCAID%253E2.3>.*

* cited by examiner

*Primary Examiner* — Jeffrey A Gaffin
*Assistant Examiner* — Nathan Brown, Jr.

(57) ABSTRACT

A method and system to evaluate image-guided dental implant treatment plans with error simulation. Error sources contributing to the inaccuracy of implant cases come from impressions, stone models, radiographic guides, CT scan and its image processing, surgical guides, as well as the surgical procedures. They are translated into the deviations between the planned and actual implant positions and orientations. The error simulation is to continuously modify and update treatment plans with the possible deviations so that the treatment plans can be visually evaluated along with other evaluation tools.

8 Claims, 10 Drawing Sheets

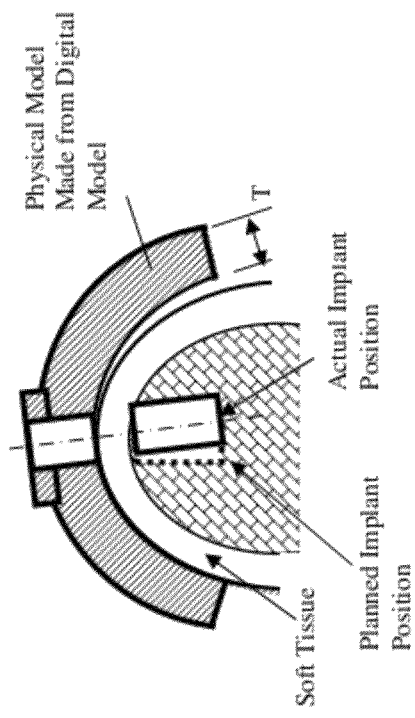
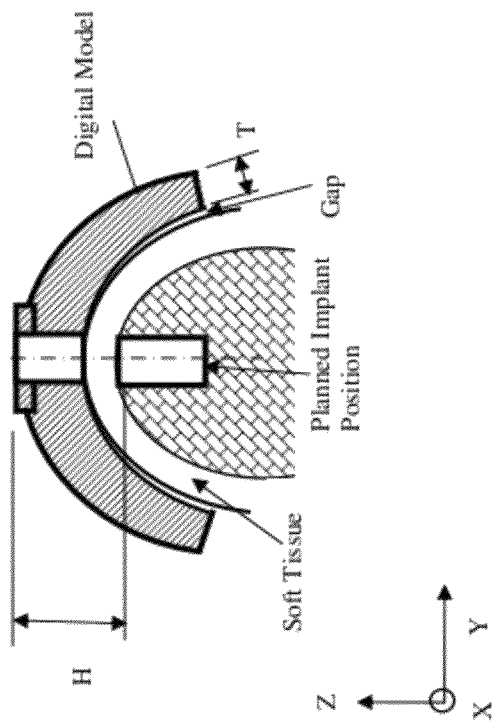
Fig. 6

ERROR SIMULATION FOR IMAGE-GUIDED DENTAL IMPLANT TREATMENT PLANNING

CROSS-REFERENCE TO RELATED APPLICATIONS

U.S. patent application Ser. No. 12/776,544 May 10, 2010 Gao

U.S. patent application Ser. No. 12/795,045 Jun. 7, 2010 Gao

REFERENCE CITED

US Patent Documents

U.S. Pat. No. 5,320,529 Jun. 14, 1994 Pompa
U.S. Pat. No. 5,538,424 Jul. 27, 1994 Gelb
U.S. Pat. No. 5,768,134 Jun. 16, 1998 Swaelens, et al.

OTHER PUBLICATIONS

Azari A, Nikzad S. Computer-assisted implantology: historical background and potential outcomes-a review. Int J Med Robot. 2008 June; 4(2):95-104.

Jabero M, Sarment D P. Advanced surgical guidance technology: a review. Implant Dent. 2006 June; 15(2):135-42.

Spector L. Computer-aided dental implant planning. Dent Clin North Am. 2008 October; 52(4):761-75, vi.

Tardieu P B, Vrielinck L, Escolano E, et al. Computer-assisted implant placement: scan template, simplant, surgiguide, and SAFE system. Int J Periodontics Rest Dent. 2007; 27(2):141-149.

Oyama K, Kan J Y, Kleinman A S, Runcharassaeng K, Lozada J L, Goodacre C J. Misfit of implant fixed complete denture following computer-guided surgery. Int J Oral Maxillofac Implants. 2009 January-February; 24(1):124-30.

Oguz Ozan, Ilser Turkyilmaz, Ahmet Ersan Ersoy, Edwin A. McGlumphy and Stephen F. Rosenstiel. Clinical Accuracy of 3 Different Types of Computed Tomography-Derived Stereolithographic Surgical Guides in Implant Placement. J Oral Maxillofac Surg 67:394-401, 2009.

Giovanni A. P. Di Giacomo, Patricia R. Cury, Ney Soares de Araujo, Wilson R. Sendyk, and Claudio L. Sendyk. Clinical Application of Stereolithographic Surgical Guides for Implant Placement Preliminary Results. J Periodontol. April 2005.

Schneider D, Marquardt P, Zwahlen M, Jung R E. A systematic review on the accuracy and the clinical outcome of computer-guided template-based implant dentistry. Clin Oral Implants Res. 2009 September; 20 Suppl 4:73-86.

Pettersson A, Kero T, Gillot L, Cannas B, Fäldt J, Söderberg R, Näsström K. Accuracy of CAD/CAM-guided surgical template implant surgery on human cadavers: Part I. J Prosthet Dent. 2010 June; 103(6):334-42.

FIELD OF THE INVENTION

This invention concerns the accuracy of the clinical outcome of image-guided implant dentistry, and the evaluation of image-guided treatment plans against possible errors. From treatment planning to surgery, many factors will lead to the inaccuracies of implant positions and orientations, which may eventually cause implant failures or difficulties in the prosthetic restorations. With error simulation, a treatment planning software system can simulate extreme error situations, evaluate treatment plans with error conditions, adjust plans, and thus lower the risk of implant failures.

BACKGROUND OF THE INVENTION

Image guided dental implant planning systems design and make surgical guides, which have drilling holes and will fit onto patients' anatomy so that the implants can be placed at the planned locations and orientations. The basic technology and procedures can be found in publications of Azari, Jabero, Spector, Tardieu, et al.

Many treatment planning users and research groups have noticed that the accuracy can be a great concern for image guided implant dentistry (Oyama, Oguz, Giovanni, et al). In a research of Schneider, et al., an electronic literature search complemented by manual searching was performed to gather data on accuracy and surgical, biological and prosthetic complications in connection with computer-guided implant treatment. From 3120 titles after the literature search, eight articles met the inclusion criteria regarding accuracy and 10 regarding the clinical performance. Meta-regression analysis revealed a mean deviation at the entry point of 1.07 mm (95% CI: 0.76-1.22 mm) and at the apex of 1.63 mm (95% CI: 1.26-2 mm). No significant differences between the studies were found regarding method of template production or template support and stabilization. Early surgical complications occurred in 9.1%, early prosthetic complications in 18.8% and late prosthetic complications in 12% of the cases. Implant survival rates of 91-100% after an observation time of 12-60 months are reported in six clinical studies with 537 implants mainly restored immediately after flapless implantation procedures.

A typical methodology of the accuracy investigation can be found in the paper of Pettersson, et al. Ten maxillae and 7 mandibles, from completely edentulous cadavers, were scanned with CT, and 145 implants (Brånemark RP Groovy) were planned with software and placed with the aid of a CAD/CAM-guided surgical template. The preoperative CT scan was matched with the postoperative CT scan using voxel-based registration. The positions of the virtually planned implants were compared with the actual positions of the implants. The mean measurement differences between the computer-planned implants and implants placed after surgery for all implants placed were 1.25 mm (95% CI: 1.13-1.36) for the apex, 1.06 mm (95% CI: 0.97-1.16) for the hex, 0.28 mm (95% CI: 0.18-0.38) for the depth deviation, 2.64 degrees (95% CI: 2.41-2.87) for the angular deviation, and 0.71 mm (95% CI: 0.61-0.81 mm) for the translation deviation. Interestingly, the results demonstrated a statistically significant difference between mandibles and maxillae for the hex, apex, and depth measurements in the variation between the virtually planned implant positions and the positions of the implants placed after surgery with a CAD/CAM-guided surgical template. Other literatures related to implant accuracy or the fit of surgical guides are found to use the similar approach. While such research does reveal some accuracy issues, the investigation method is problematic. The researchers usually have only one or two systems, they usually don't try to address where the errors are from by looking at the workflow and image processing approaches, and moreover the research procedures like the afterward registration mentioned above can introduce errors as the treatment planning software does.

The errors of surgical guides come from the design and manufacturing process. The prior art to make surgical guides can be found in Pompa U.S. Pat. No. 5,320,529, Gelb U.S. Pat. No. 5,538,424, Swaelens U.S. Pat. No. 5,768,134, and Gao's U.S. patent application Ser. Nos. 12,776,544, 12,795, 045. The published software systems, such as SimPlant™, NobelGuide™, EasyGuide™, etc, utilize similar techniques. Swaelens described the commonly used method, which features so called 'Dual Scan' and surgical guide made by SLA. The dual scan protocol uses a radiographic guide that has radiographic markers. A patient is CT-scanned wearing a radiographic guide, and then the guide is scanned separately. The two CT scan datasets are loaded and registered together. Implants are simulated with the patient CT scan, and drill holes are made on the digital model of the radiographic guide, which results in a surgical guide. The surgical guide is later on made with SLA or 3D printing technology. Any manufacturing or data processing error in this workflow can lead to the inaccuracy or misfit of the surgical guide.

Some conclusions one can draw from the workflow and the research in the guide accuracy area are: some errors are inherent to the workflows and underlying technologies; depending on patients' oral-dental structures and the restoration techniques, some cases can tolerate bigger inaccuracy, some cannot; even though the errors of 1 mm or more sounds substantial, the implant survival rate is actually good; more work needs to be done to better breakdown the error sources, and tackle the accuracy issues one by one, or to improve the workflows; since errors can not be avoided or hard to control, it can be very beneficial to evaluate a plan against maximum error conditions. This disclosure is relevant to the evaluation of treatment plans as errors are concerned.

The placement of an implant is often evaluated in a few ways. The most common tool is so-called bone quality analysis. The neighborhood bone structure of an implant is displayed with a color scheme so that the CT Hounsfield unit values are mapped into different colors. The users can justify the sufficiency of bone structure by looking at the neighborhood colors. In addition, a safety zone can be defined for an implant, which is typically a 2-3 mm offset of the implant surface. It is mainly used to check the interferences between an implant and adjacent teeth, other implants or nerve channels.

In the published systems, the evaluations of treatment plans do not include "what-if" simulations, or error simulations. The objective of this invention is to introduce a mechanism to simulate various error conditions, and integrate such error simulation into the evaluation process of a treatment plan.

BRIEF SUMMARY OF THE INVENTION

The data representation of a treatment plan includes the coordinates of apex centers and the orientation vectors of all the implants. A plan is visualized in 2D and/or 3D views. Along with the bone structure, or even soft tissue models, users can visually evaluate a plan.

Error simulation is done by continuously applying different deviations to the implant parameters and updating the plan display accordingly. First, error sources are identified. A few examples are errors of stone models, manufacturing errors and deformations of radiographic guides, errors of radiographic guide placements, errors of CT image processing, etc. Secondly, each error factor is translated into the possible deviations of implant locations and orientations. Maximum deviation values are set for each of the factors. Next, a statistic distribution of the errors is assumed, and a series of deviation values are generated. For each deviation value, the display of a treatment plan is updated. With continuous update of the display, a real time visual feedback is given to the users so that they can evaluate the plan and possible error conditions. Such error simulation is coupled with techniques such as bone quality visualization to enable better treatment plan evaluation.

The software component or system to simulate the error conditions includes the following logical components: an interface object (such as a file or a dialog) to designate the error factors and their distributions, a module to combine the error factors and generate a series of positions and orientations for each implant, a module to display treatment plan and update the display with the series implant positions and orientations, and a module to control the error simulation.

DESCRIPTION OF THE DRAWING

FIG. 6. Implant deviation (angular deviation) caused by the error of the digital model of a radiographic guide, or any model that is intended to be used as a base for surgical guide. The digital model with geometric errors is physically made and used as surgical guide. The changed shape can lead to the misfit of the surgical guide.

FIG. 12. A possible integration of error simulation with other plan evaluation tools. Other evaluation tools can generally not run when the error simulation is going on.

DETAILED DESCRIPTION OF THE INVENTION

The Method

Figure 1:
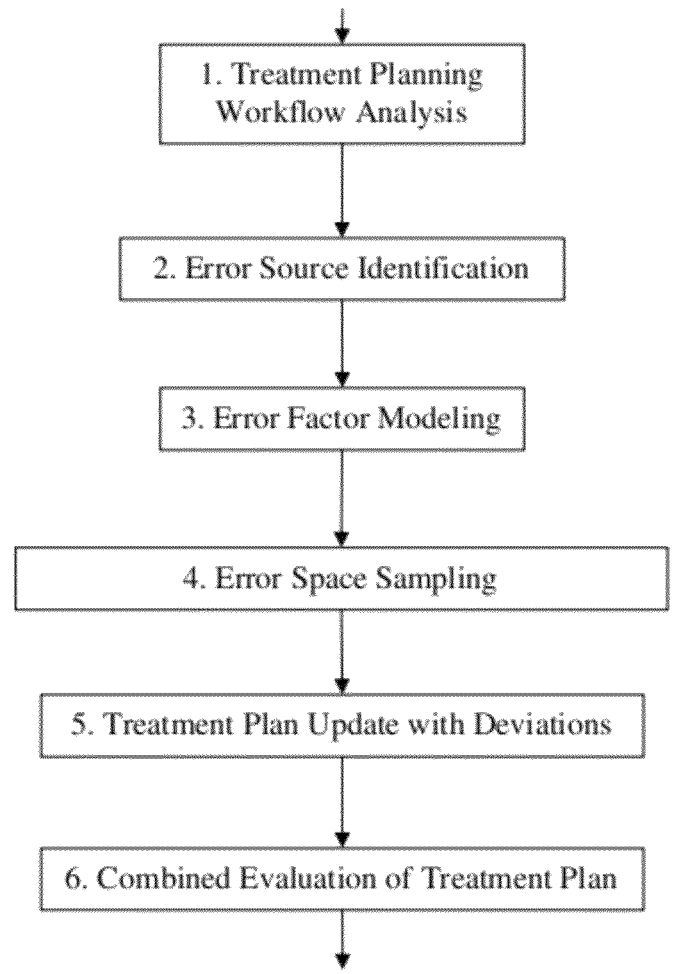
FIG. 1. The steps of error simulation for a dental implant treatment planning software. First, the workflow is analyzed, error factors are identified. Then a mathematical model—"error space"—of the error distribution is defined or chosen, and possible errors are generated by sampling the "error space". Finally the treatment plan is updated with various error values, and evaluated with error simulation along with other plan evaluation tools.

The disclosed approach to error simulation for dental implant treatment planning is illustrated in FIG. 1. It has the following steps. (1) treatment planning workflow analysis; (2) error source identification; (3) error factor modeling; (4) error space sampling; (5) treatment plan update with deviations; (6) combined evaluation of treatment plans.

The first element in this workflow is to analyze the treatment planning workflow focusing on possible error sources. With any planning workflow, there are essentially two data sources, or error sources. The first is the patient CT scan, which is used to evaluate bone density and dental structure, and to identify the locations to place implants. Bone structures, nerve channels, tooth models, etc. can be segmented or created from patient CT scan to help determine implant parameters. Another data source is the anatomy surface where the surgical guides will fit onto. For a flapless surgery, this includes soft tissue and remaining tooth surfaces. For a flap surgery, this will be the combination of the bone surface and remaining teeth. This surface is used to design the surgical guides so that the implant holes can be drilled as expected. Since the implants are placed with respect to the bones, this surface model will need to be transformed into the coordinate system of the bone model of the CT scan and aligned with the bone. This transformation is called registration.

Figure 2:
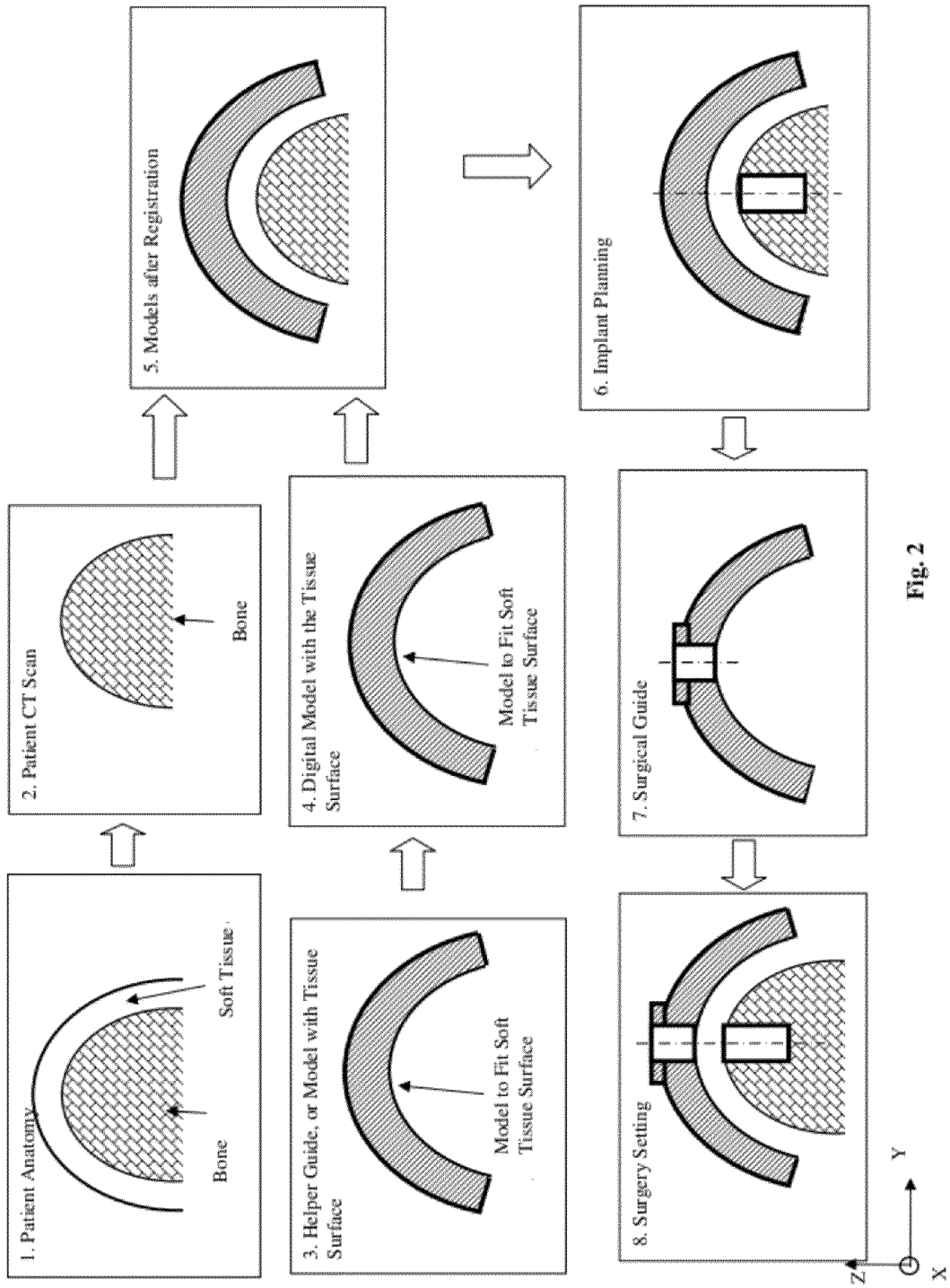
FIG. 2. A generalized workflow of implant treatment planning, wherein each step can contribute to the inaccuracy of the final actual implant positions and orientations. This is a generalized description of so-called "Dual Scan" protocols found in almost all image-guided dental implant planning software systems.

Using two data sources for treatment planning is a generalization of any actual workflows. It is illustrated in FIG. 2. The first box labeled "Patient Anatomy" shows bone and soft tissue of a fully edentulous case. For partially edentulous cases with remaining teeth, the ideas are the same. The patient CT scan is shown in box 2, which has a segmented bone structure. Soft tissues are not possible to model with patient CT scan. Instead, a procedure in box 3 and 4 is used to obtain the soft tissue model. In box 3, a helper guide is made to fit onto patient's soft tissue, therefore the inner surface of this helper guide represents the soft tissue surface. Box 4 shows the digital model of this helper guide. The helper guide can be for example radiographic guide, impression, etc. Box 5 is a combination of the bone model and the helper guide. Registration is used to align the two models together. With various embodiment of the helper guide in box 3, there can be various approaches for this registration. Next, the treatment is planned with the combined model in box 6, and the shape of the helper guide is modified with the form features that will guide the drills in box 7. This modified version of the helper guide is eventually made and used as surgical guide in box 8.

In order to obtain the second data source—the helper guide in FIG. 2, various ways have been explored, such as radiographic guides, intro-oral scans, plaster models, etc. There can be many variations of such a workflow, but the concepts are the same.

Any errors in the preparation and processing of the data sources can lead to the inaccuracies of implant locations. Take the approach using a radiographic guide as example, which is a common practice of FIG. 2. Its procedure is listed below. Any of the steps can cause errors. With all these factors coexist, it is not practical to predict how accurate a surgical guide will be, or a surgery will be.

1. An impression is taken first.
2. A plaster model is made using conventional lab approach.
3. A radiographic guide is then made with the plaster model.
4. The patient is then CT scanned wearing the radiographic guide.
5. The guide is scanned separately in order to get a clear surface model that fits the patient anatomy.
6. The two sets of scan data are loaded into a software system and aligned together.
7. A digital surface model of the radiographic guide is generated from its CT scan.
8. Implant placement is simulated with reference to both the bone structure and radiographic guide.
9. Drilling holes are created on the radiographic guide model, and some other form features are also added to the model. This results in the surgical guide model.
10. The surgical guide is made with SLA or milling.
11. The surgical guide is placed onto patient's dental structure for a surgery.

After the workflow analysis, error factors can be listed and compared. The most influential factors will be identified for further processing. Examples of those factors include the error of CT scan segmentation, the error of registration, the error of surgical guide deformation, etc.

Figure 3:
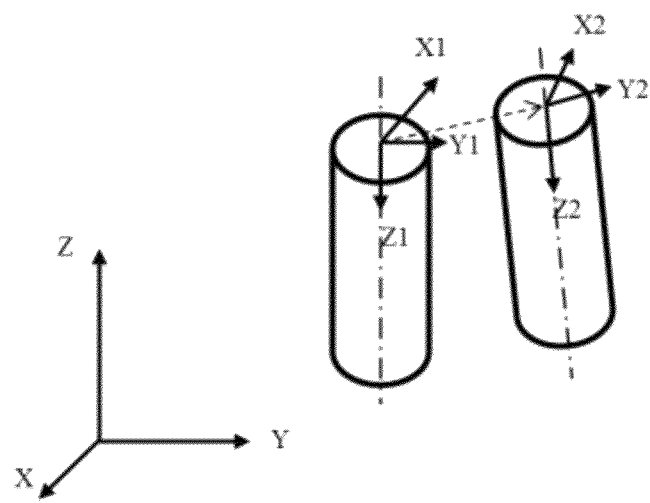
FIG. 3. An illustration of implant deviation.

The next element of error simulation workflow in FIG. 1 is the modeling of error factors. An error source is first translated into the deviations of implant positions and orientations, or simply, the deviations. FIG. 3 shows an implant and its deviation. A linear error means the shifts of X, Y and Z coordinates, notated as (dx, dy, dz). An Angular error means the deviation of the implant orientation. An angular deviation can be a combination of rotations about X, Y and Z axis. Normally the rotation about Z axis does not really change implant position, hence the rotations about the X and Y axis are considered and represented by two angles: angle_x, angle_y. The deviation between two implants has therefore 5 components and is represented as (dx, dy, dz, angle_x, angle_y). These 5 components define a 5D space, namely, error space.

Figure 4:
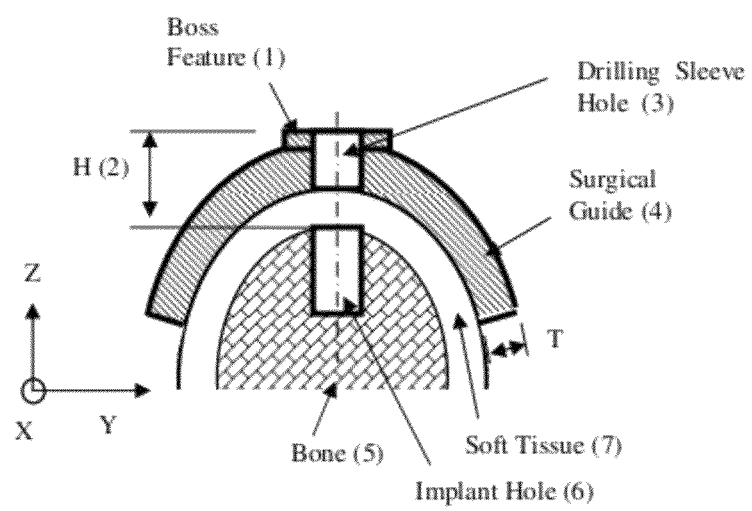
FIG. 4. An illustration of flapless image guided implant placement. A surgical guide with drill sleeves are placed onto a patient's mucosa. Implant holes can be drilled with the guidance of the sleeves.
Figure 5:
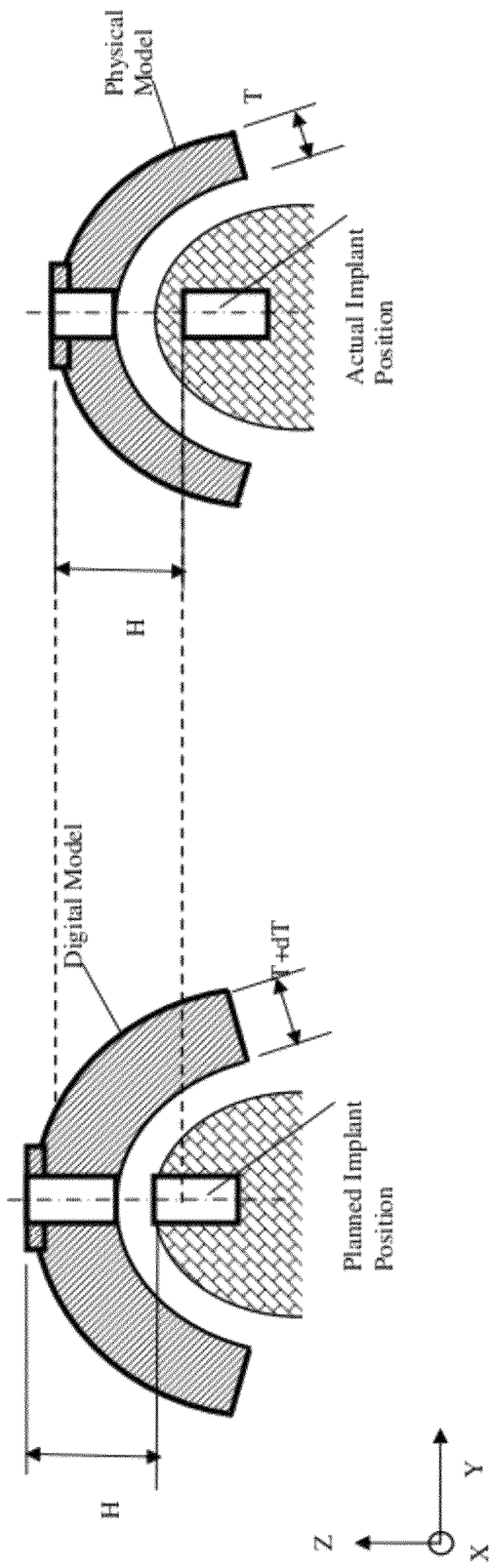
FIG. 5. Implant deviation (position shift) caused by the error of the digital model of a radiographic guide, or any model that is intended to be used as a base for surgical guide. Treatment planning is done with this digital model, but the surgery is performed with the modification of the original physical model. The difference of the thickness of the two models leads to the deviation of the implant hole.

Each individual error factor can contribute to the 5 components in a different way. FIGS. 4 and 5 illustrate a treatment plan with one implant, and how the error of the guide thickness will cause implant deviation. FIG. 4 is the nominal situation. The surgical guide 4 is designed from radiographic guide model by adding the drilling hole 3 and a boss feature 1 at the top. The top planar face is supposed to have a fixed distance H from the top of the implant. The implant hole 6 is where the implant will be eventually placed, which is drilled with the guidance of the drilling hole 3. The radiographic guide has a thickness T, which can vary from point to point. For the sake of simplicity, the guide thickness is considered uniform.

The digital model of the radiographic guide comes from its CT scan. Due to the nature of image processing and contouring algorithm, the digital model may not match the actual size. We use the error of the thickness to represent the error of this digital model for the sake of simplicity. The surgical guide can be made directly with the physical model of the radiographic guide, or from this digital model.

If the surgical guide is made with the physical model of the radiographic guide, such as the approach of EasyGuide™, the error of the thickness T will cause the vertical deviation of the implant hole, as illustrated in FIG. 5. The left part of this figure is the planned implant and the digital model of a radiographic guide that has an error. The right side is the scenario that the actual physical model of the radiographic guide is converted into the surgical guide. The physical model has a thickness of T, but the digital model is T+dT. The top boss feature is design based on T+dT with the model in the left side. When the guide is actually applied onto patient's mouth, the actual top face will be lower than the planned place by dT, so is the implant location.

If the surgical guide is made from the digital model (Swaelens U.S. Pat. No. 5,768,134), this vertical deviation caused by the afore-mentioned thickness error can be avoided, because the thickness of the model used in planning is same as the physical model, even though not same as the original radiographic guide. Due to this thickness error, the model's inner face can not actually fit onto the soft tissue. There might be a gap or shape error as illustrated in FIG. 6. When the surgical guide is used in surgery, the guide can be positioned as shown in the right side of this picture, which has an angular deviation about X axis, and also a shift of the implant apex. A mathematic relationship can be established between the dimension of the gap and the deviation of the implant.

Similarly other error factors can be analyzed and translated into certain formulas of the five components of implant deviation. The analysis described above indicates that the error factors contribute to the implant deviations in a different way if the treatment planning workflows or manufacturing approaches are different.

Another aspect of the error modeling in FIG. 1 is to have a statistic model of the error distributions. For example, it is assumed that the thickness error dT in FIG. 5 has a maximum value of v, minimum value of 0, and it's simply linearly distributed in the range of (−v, v). In other words, the probability of the implant deviation at any value within this range is same. A more advanced statistic distribution and probability model can be established.

Similarly, for each error factor, its contribution to the five components of a deviation can be therefore defined as certain extreme values. In other words, each error factor's range can be defined as a 5D box in the error space. With the linear distribution assumption, such 5D boxes corresponding to all the error factors can be combined into a maximum bounding box, which is the entire deviation range of a treatment plan. Any point in this bounding box defines a possible error scenario.

In the step 4 of the workflow of FIG. 1, the error ranges of each deviation component are then used to generate sample points in this error space. For example, the value of x—the X deviation of implant apex—can be any number within (−maximum_dx, maximum_dx). Assuming the sampling rate is N, i.e., N points are sampled in each component dimension, a total of $N^5$ samples can be calculated. As a result of this error space sampling, a series of possible deviations are generated.

Figure 7:
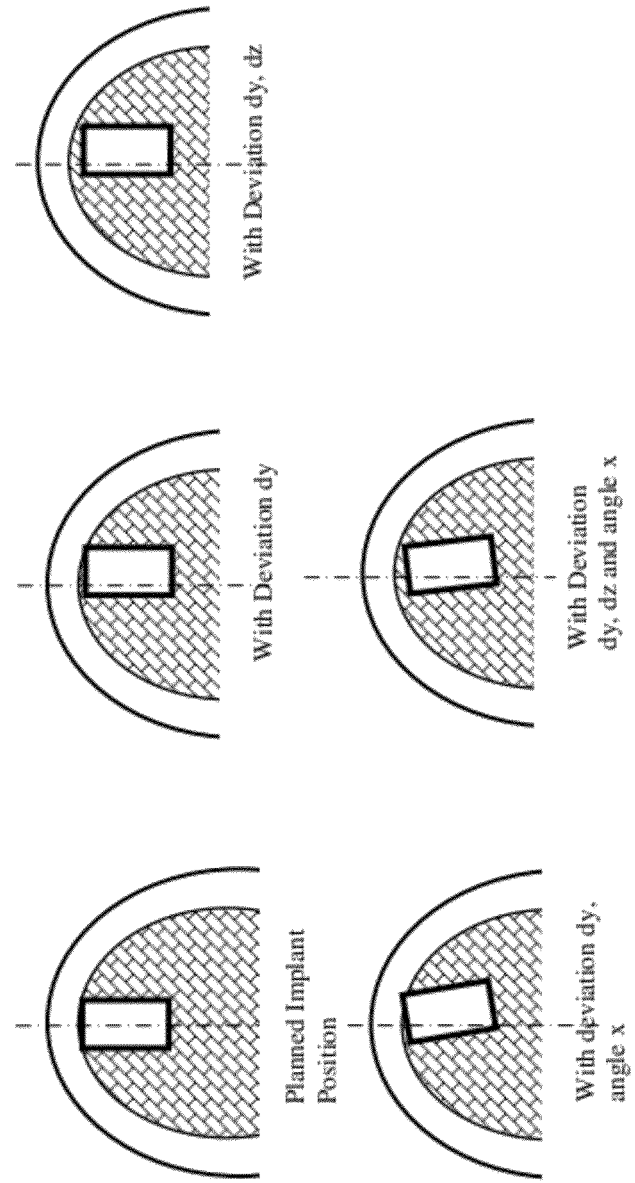
FIG. 7. A series of implant deviations.
Figure 8:
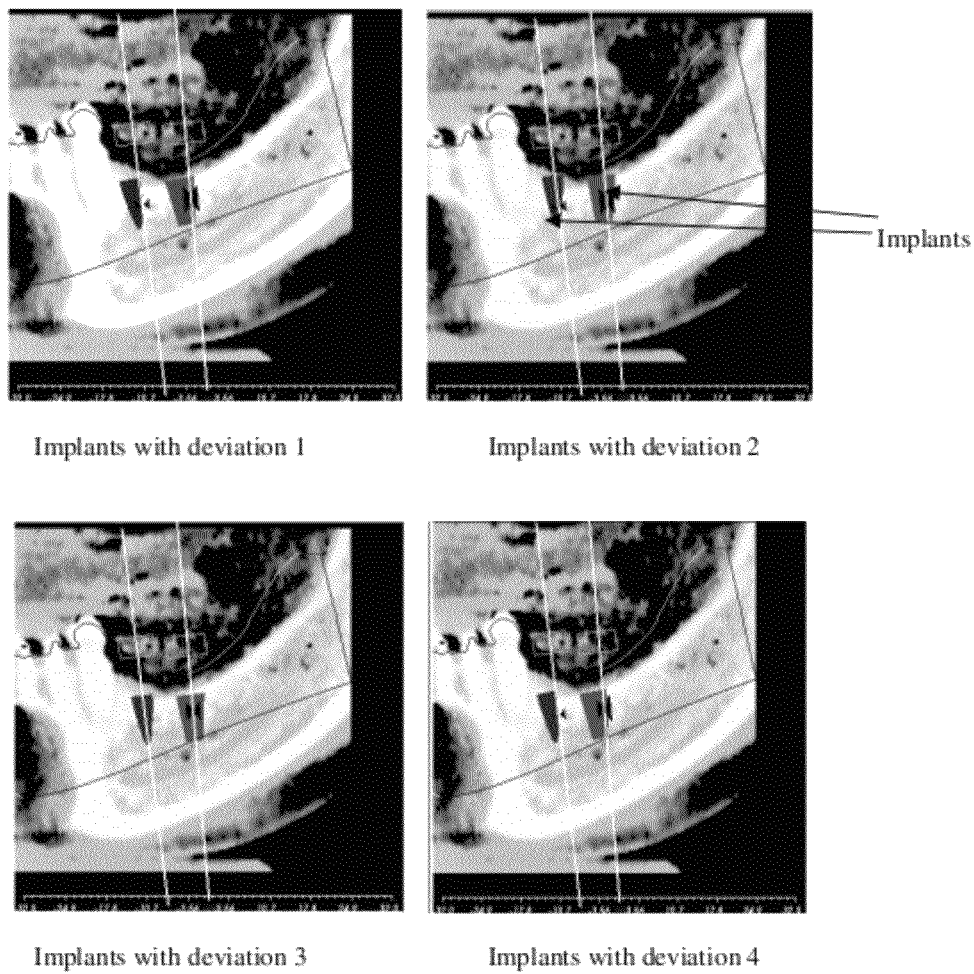
FIG. 8. Screenshots of implant deviations, where each of the pictures is corresponding to one possible error condition.

The errors can be then simulated by updating the display of the treatment plans with the possible deviations. For each of the sample point in the error space and for each implant in a treatment plan, the models and displays are updated. FIG. 7 illustrates a series of implant positions corresponding to different error values. FIG. 8 shows screenshots with 2D slices and the implants with the errors simulated. With the implant positions and orientations being updated in a real time, the users have a good feedback about how implants may interact with adjacent teeth and implants, as well as the bone structure. In this case, the implant at certain possible deviation can interfere with the bone area with relatively high density, which will cause difficulties for the actual drilling. Therefore the simulation suggests that the treatment plan needs adjustment.

Further on, the evaluation of a treatment plan can combine error simulation and other methods to evaluate plans, which is the last step in the workflow of FIG. 1. There are two aspects with this step. The first one is to integrate error simulation into the workflow of treatment plan evaluation. The second aspect is how error simulation is integrated with other tools. This is more related to the software embodiment, and will be elaborated in the next section.

The System

Figure 10:
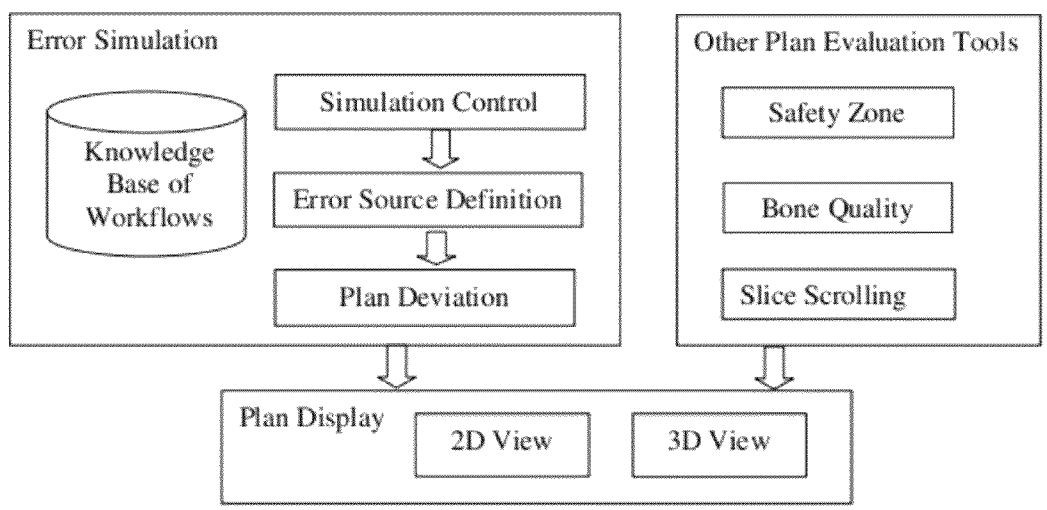
FIG. 10. The software architecture of a treatment plan evaluation and error simulation system. The error simulation changes treatment plans with small deviations, while other evaluation tools change the way the treatment plans are displayed. Together they make a complete evaluation paradigm.

A software system or module with error simulation is illustrated in FIG. 10. Error simulation and other evaluation tools cause the update of the display of a treatment plan in both 2D and 3D views. While other evaluation tools such as "Bone Quality" and "Safety Zone" change the display of a specific plan, the error simulation is the only tool that provides "What-if" evaluation of a plan.

Figure 11:
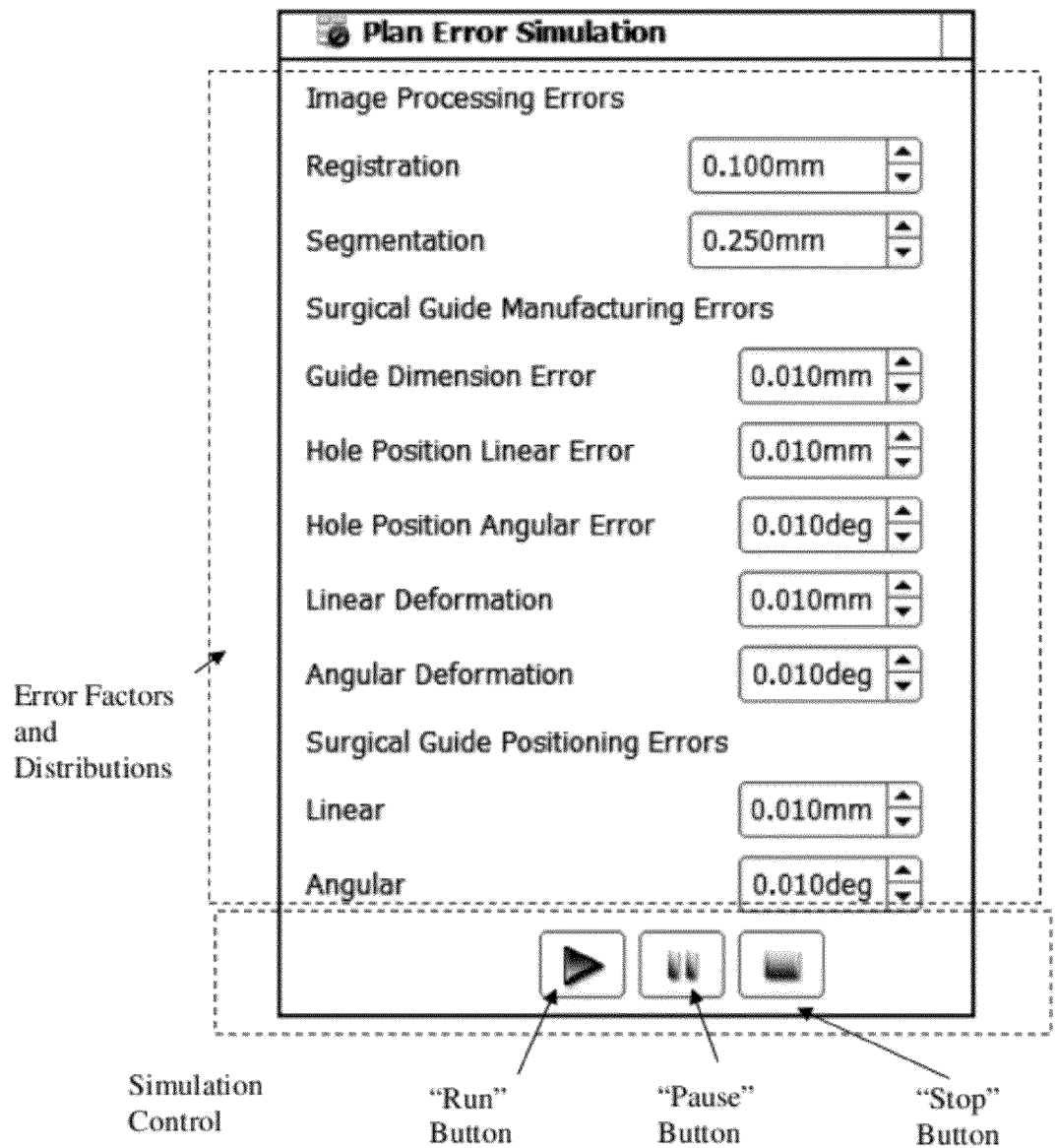
FIG. 11. A dialog to define error factors and control the simulation. Each error source is defined by its maximum contribution to implant deviations. A linear distribution is assumed by this dialog. Buttons are also included in this dialog to control the execution of the error simulation.

FIG. 11 illustrates a dialog—an embodiment of the interface to define error factors and to control the simulation. A few major error items are listed in the dialog. Errors from image processing include registration and segmentation errors. Errors from surgical guide manufacturing include the guide dimension errors, implant hole positional and angular errors, as well as the deformation of the surgical guide that is mainly applicable for guides made with SLA or 3D printing. Errors of the surgical guide positioning reflect how well the placement of the surgical guide can repeat the position of the radiographic guide when it is scanned.

In this dialog, the errors are defined and implemented as deviations of the implant positions and orientations. The values in this dialog are the maximum values of the corresponding items. Another aspect of the workflow indicated in this dialog is a simplified embodiment that the errors are assumed to be evenly distributed in their value ranges.

This error source definition is backed by a workflow knowledge base, which contains the rules or data regarding to what error factors need to be considered for an underlying case, and what are the range of the deviations caused by the each error factor.

Another component of the error simulation module of FIG. 10 is "Plan Deviation", which generates possible deviations according to the error source definition and statistic distributions, and applies them to the treatment plan. Each component of the deviation, for example the dx component, will have a series values: −maximum_dx, −(N−1)-maximum_dx/N, . . . , −maximum_dx/N, 0, maximum_dx/N, . . . , (N−1)-maximum_dx/N, maximum_dx. The combinations of the series values of each component together make up the sampling space of the implant deviations. The "Plan Deviation" module may generate all the combinations in one run, or individually upon request.

This "Plan Deviation" module then applies the deviations to a treatment plan by transforming the geometric models of the implants. For each implant and a specific deviation value (dx, dy, dz, angle_x, angle_y), it (1) stores the coordinates (x, y, z) of the implant apex, (2) translates the implant model by (−x, −y, −z) so that the apex is positioned at the origin, (3) rotates the implant model by angle_x about X axis, (4) rotates the implant model by angle_y about Y axis, (5) and finally translates the implant model by (x+dx, y+dy, z+dz).

The "Plan Display" module will receive the deviated plans from "Plan Deviation" and update the display by using transformed implant models. The minimum of the display contents include bone and implants. There are at least two kinds of display windows, ie., the 3D views and 2D views.

Figure 9:
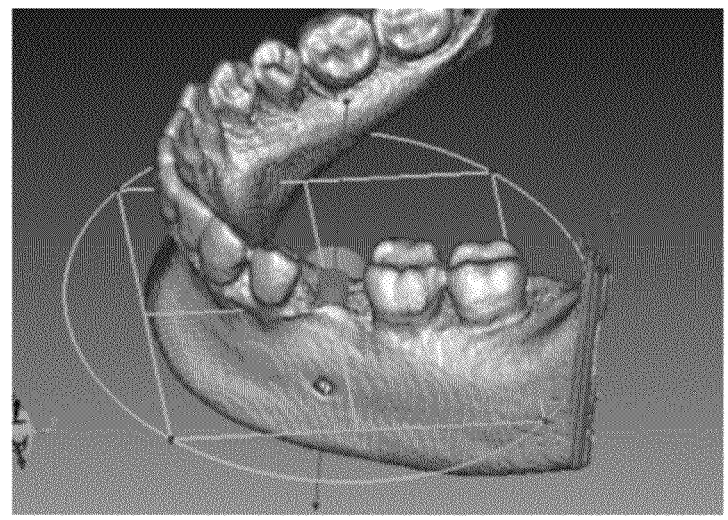
FIG. 9. 3D view of an implant deviation along with bone model.

For each of the views, there can be many display options coming from other tools of plan evaluation, such as black/white display, color maps, transparency, slice scrolling, etc. FIGS. 8 and 9 shows the 2D black and white slices and 3D pictures.

Figure 12:
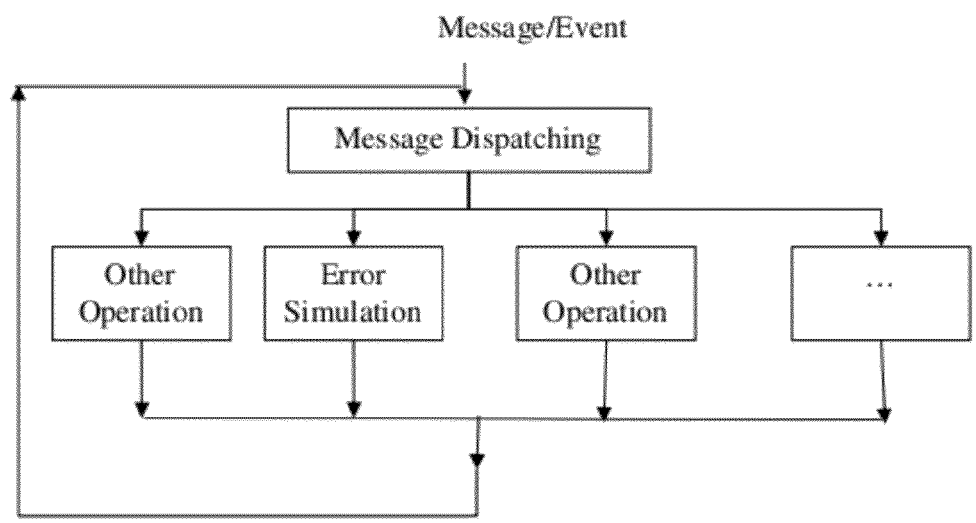

In FIG. 10 there is a "Simulation Control", which not only controls the actions like "Start", "Pause", "Resume", etc. as shown in FIG. 11, but also manages the way the error simulation is integrated with the entire treatment planning software. This integration has two options. In option 1, a single threaded method is used. Once the simulation starts, it will run through all the possible deviations one by one in predefined order and the user can not interfere with the process. This workflow is illustrated in FIG. 12. Error simulation is just one of the action callbacks responding to the user interactions.

In option 2, the error simulation can interweave with other evaluation tools. A specific embodiment that integrates error simulation, bone quality and slice scrolling together in 2D views works this way: the 2D slices are shown with colors mapped to the bone density; the implants are moved from one position to another to reflect different deviations; in the mean time, the 2D views change their slices from one to another showing a series of slices corresponding to the size of the implants, and possibly in the meantime, the user can change the display by zooming, rotating, and other options. Such continuous updating of the display provides a very helpful tool for the users to evaluate the various implant locations and their neighborhood bone quality. Therefore the major differentiator of this approach is that other operations—mainly plan evaluation operations—can be injected into the series of display updates corresponding to the implant deviations generated for error simulation.

Figure 13:
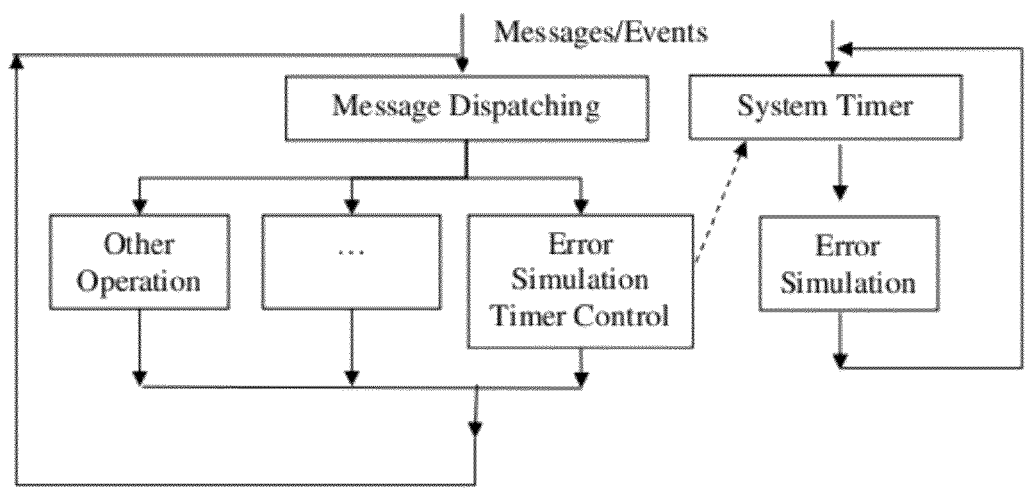
FIG. 13. Another possible integration of error simulation with other plan evaluation tools. The error simulation is running in a separated thread controlled by a timer, and other evaluation tools can be interwoven with error simulation through the injection of corresponding events/messages in the event loop or message queue.

A specific embodiment is illustrated in FIG. 13. In order to realize such an interweaving plan evaluation process, a system timer is used to control the error simulation module. The timer will trigger a call to the update code at predefined time interval in certain amount of milliseconds. Each call will transform all implants to their next positions according to the deviation values. Between the intervals of the timer, users can perform other operations while the simulation is going on unless there is a conflict. For example, the operations like zooming and rotating can be invoked, and injected into the event loop. The user can scroll the 2D slices through the slice range of an implant, or even through all the slices of the CT scan. One or more of such operations will be executed between any two consecutive updates of implant display of the error simulation. The user interface of the simulation control can also pause, stop and kill the timer so that the error simulation can be controlled accordingly. The error simulation module is controlled by the timer in a separated thread, and the timer is controlled by the "Error Simulation Timer Control", which is essentially a few buttons in the user interface. The event or message processing for this timer control will return right away after a command is sent to the timer, which will allow the users to perform other operations when the simulation is running.

What is claimed is:

1. A computer system for dental implant treatment planning that simulates various error conditions before actual surgery, comprising:
 1) a computer hardware system with an operating system,
 2) an interactive computer software that is saved to a non-transitory computer readable medium, which generates images and graphics shown on a display of the computer, and performs treatment planning error simulation, wherein:
  a) a software interface is used to obtain a desired treatment plan of all the implants in a treatment planning case,
  b) a plan display module is provided to display treatment plan with 2D and 3D views, where
   (1) the display at least comprises of implants and bone structures,
   (2) display options comprise of black/white display, color map of the CT Hounsfield Unit values, transparency and 2D slice scrolling, and
   (3) plan evaluation tools are provided together with the display,
  c) an error simulation module is provided to perform simulation, comprising
   i. an error source definition module to specify various error sources that exist in both the treatment planning, surgical guide manufacturing and actual treatment and can cause the actual outcome of a treatment to be off the treatment plan,
   ii. said error sources are translated into five components of an implant positional deviation,
   iii. a statistic distribution is assigned to the error sources,
   iv. a plan deviation module to generate variations of said treatment plan by continuously applying different deviations to the implant parameters, and
   v. a simulation control module to control the said deviation module with "Start", "Pause" and "Resume" actions, and send its outputs to said plan display module,
whereby the computer system can continuously modify and update treatment plans with the possible deviations so that doctors can visually evaluate and adjust the treatment plans for the best implant positions and orientations even before the treatment is performed, and thus lower the risk of implant failures.

2. The computer system of claim 1, wherein
 1) said implant treatment plan is defined as the coordinates of apex centers and the orientation vectors of all the implants, as well as implant shape and dimensions of the case, and
 2) an implant planning user interface is provided to acquire the treatment plan.

3. The computer system of claim 1, wherein said error source definition module further
 1) lists a set of possible error sources for users to specify,
 2) translates each error source into possible deviations of implant locations and orientations,
 3) sets maximum deviation values for every error sources,
 4) defines said statistic distribution of each error, and
 5) generates a series of deviation values for the positions and orientations of every implants.

4. The computer system of claim 3, wherein the error source definition module further has a process that
 1) an error source is translated into five components of an implant deviation including the shifts in x, y and z directions, and rotation angles about x and y axis of the implant itself,
 2) said components define a 5 dimensional space referred as error space,
 3) an error range of said error source is defined as a 5D box in said error space, and
 4) the error source is defined as linear distribution within said 5D box,
 5) said 5D boxes of all the error factors are merged together, which produces the combined error ranges for all the implants,
 6) an algorithm is provided to perform error space sampling for said 5D boxes, which generates possible combinations of implant deviations.

5. The computer system of claim 1, wherein the error source definition tool comprises software interface to specify
 1) image processing errors,
 2) surgical guide manufacturing errors, and
 3) surgical guide positioning errors.

6. The computer system of claim 1, wherein
1) a simulation control module comprising a system timer is used to run, pause, resume, stop and cancel the error simulation, and
2) user interface tools comprising the functional elements of "start", "pause", "resume" and "stop" are provided to control the timer interactively.

7. The computer system of claim 1, wherein
1) plan evaluation tools or display tools are available while the error simulation is running, wherein
   a. the 2D slices are shown with colors mapped to the bone density,
   b. the implants are moved from one position to another to reflect different deviations, and
   c. in the meantime, the 2D views change their slices from one to another showing a series of slices corresponding to the size of the implants, and the user can change the display by zooming, rotating, and other options to evaluate the various implant locations and their neighborhood bone quality,
2) the computer system's responses to said evaluation or display tools are injected into the system event loop, and executed between series of updates of the error simulation.

8. The computer system of claim 1, wherein said plan deviation module
1) generates all the combinations of the implant errors,
2) applies the deviations to a treatment plan by transforming the geometric models of the implants,
3) sends deviated treatment plans to said plan display module, where the implants are continuously transformed and displayed according to the deviations, whereby once the simulation starts, it will run through all the possible deviations one by one in predefined order and the user cannot interfere with the process.

\* \* \* \* \*